United States Patent
Fago et al.

(10) Patent No.: US 7,998,133 B2
(45) Date of Patent: Aug. 16, 2011

(54) DISPOSABLE FRONT LOADABLE SYRINGE AND INJECTOR

(75) Inventors: Frank M. Fago, Mason, OH (US); Frank M. Lewis, Fairfield, OH (US)

(73) Assignee: Mallinckrodt Inc., Hazelwood, MO (US)

( * ) Notice: Subject to any disclaimer, the term of this patent is extended or adjusted under 35 U.S.C. 154(b) by 487 days.

(21) Appl. No.: 12/107,988

(22) Filed: Apr. 23, 2008

(65) Prior Publication Data

US 2008/0215007 A1 Sep. 4, 2008

Related U.S. Application Data

(63) Continuation of application No. 10/990,587, filed on Nov. 17, 2004, now abandoned.

(51) Int. Cl.
*A61M 25/16* (2006.01)
(52) U.S. Cl. .................................. 604/533; 604/154
(58) Field of Classification Search .............. 604/131, 604/181, 523, 533, 154
See application file for complete search history.

(56) References Cited

U.S. PATENT DOCUMENTS

| | | |
|---|---|---|
| 5,047,021 A | 9/1991 | Utterberg |
| 5,071,413 A * | 12/1991 | Utterberg ............ 604/533 |
| 5,300,031 A | 4/1994 | Neer et al. |
| 5,383,858 A | 1/1995 | Reilly et al. |
| 5,451,211 A * | 9/1995 | Neer et al. ............ 604/154 |
| 5,535,746 A | 7/1996 | Hoover et al. |
| 5,658,261 A | 8/1997 | Neer et al. |
| 5,738,659 A | 4/1998 | Neer et al. |
| 5,997,502 A | 12/1999 | Reilly et al. |
| 6,017,330 A | 1/2000 | Hitchins et al. |
| 6,027,482 A | 2/2000 | Imbert |
| 6,200,289 B1 | 3/2001 | Hochman et al. |
| 6,368,307 B1 | 4/2002 | Ziemba et al. |
| 6,402,718 B1 | 6/2002 | Reilly et al. |
| 6,432,089 B1 | 8/2002 | Kakimi et al. |
| 6,475,192 B1 | 11/2002 | Reilly et al. |
| 6,527,742 B1 | 3/2003 | Malenchek |
| 6,652,489 B2 | 11/2003 | Trocki et al. |
| 2004/0064041 A1 | 4/2004 | Lazzaro et al. |
| 2004/0116861 A1 | 6/2004 | Trocki et al. |
| 2004/0133153 A1 | 7/2004 | Trocki et al. |

(Continued)

FOREIGN PATENT DOCUMENTS

WO WO03095000 A1 11/2003

OTHER PUBLICATIONS

ISO 594-2: "Conical Fittings with a 6% (Luer) Taper for Syringes, Needles and Certain other Medical Equipment—Part 2: Lock Fittings"; May 1, 1991, IDS-594-2, pp. I-II, 1, XP000826443 abstract; Figures 1-2.

(Continued)

*Primary Examiner* — Nicholas D Lucchesi
*Assistant Examiner* — Laura A Bouchelle
(74) *Attorney, Agent, or Firm* — Wood, Herron & Evans, LLP

(57) ABSTRACT

A syringe for an injector that has at its nozzle end a connection to the fluid delivery tubing that prevents, reduces, or eliminates fluid leaks, by virtue of a ridge on the external surfaces of the connector which engage to tubing. Furthermore, the syringe and injector are configured to permit the syringe to be oriented in more than one manner on the injector.

13 Claims, 10 Drawing Sheets

U.S. PATENT DOCUMENTS

2004/0133161 A1 7/2004 Trocki et al.
2004/0133162 A1 7/2004 Trocki et al.
2004/0143224 A1 7/2004 Field et al.
2005/0251096 A1 11/2005 Armstrong et al.
2006/0058734 A1 3/2006 Phillips

OTHER PUBLICATIONS

International Search Report, Corresponding Application No. PCT/US2005/042313, Mailed May 23, 2006.

* cited by examiner

DISPOSABLE FRONT LOADABLE SYRINGE AND INJECTOR

CROSS REFERENCE TO RELATED APPLICATION

This application is a continuation of U.S. application Ser. No. 10/990,587, filed Nov. 17, 2004, which is incorporated herein in its entirety.

FIELD OF THE INVENTION

The present invention relates to disposable replacement syringes for patient fluid injectors and adapters for a fluid injector to accept the syringe.

BACKGROUND OF THE INVENTION

Injectors are devices that expel fluid, such as contrasting media, from a syringe and through a tube into a patient. The injectors are provided with an injector unit, usually adjustably fixed to a stand or support, having a drive that couples to the plunger of the syringe to drive it forward to expel fluid into the tube, or that may be driven rearward to draw fluid into the syringe to fill it. Usually the syringe is a disposable replacement type.

In the injection phase where the plunger is driven forward, pressures are developed in the syringe that range from, for example, 25 psi for some applications to over 1000 to 1200 psi for other applications. Syringes that contain fluid under the higher range of pressures are expensive and therefore can be impractical where the syringes are disposable. Thus, many injectors for high pressure applications have been provided with pressure jackets that are fixed to the injector units and into which the syringes are inserted. The pressure jackets contact the outer surfaces of the syringe to restrain the walls of the syringe against the internal pressures. Other syringes for lower pressure use do not have a pressure jacket.

The injectors described in U.S. Pat. No. 5,300,031; U.S. Pat. No. 5,451,211; and U.S. Pat. No. 5,658,261 use a syringe that must be oriented to a single position to orient the nozzle and tubing connector when the syringe is loaded in the injector. This required orientation hinders rapid attachment and replacement of the syringe. In addition, although the Luer connection, syringe/tubing connection, described in the above patents may be adequate for injector applications that use low pressures, leaks often occur when high pressure applications are used. Power injectors require the connection of the Luer lock system to be effective for pressures up to 1,200 p.s.i. Some users have attempted to remedy the leak problem by tightening the connection as much as possible. Over-tightened Luer connectors sometimes crack which compromises the seal. Another problem is that sometimes the connection sticks and the Luer lock cannot be disassembled.

Hence, there has been a need to more quickly load and unload disposable replacement syringes in injectors, and for injectors and replacement syringes that can accommodate a more efficient process of syringe replacement. There is also a need for a fluid tubing delivery system, such as a Luer lock system, that does not leak when used with power injectors.

SUMMARY OF THE INVENTION

The present invention provides injectors, syringe interfaces and syringes that address the needs for rapid loading of syringes and the prevention or elimination of fluid leaks between the syringe nozzle and fluid delivery tubing connection, a Luer lock connection. Specifically, the present invention provides a syringe for an injector that has at its nozzle end a connection to the fluid delivery tubing that prevents, reduces, or eliminates fluid leaks. The syringe can also be oriented in more than one manner on the injector.

Another objective provides a syringe adapter, interface, or rotatable cam that can be retrofitted to the faceplate of the injectors to engage a notch at the proximal end of the syringe casing (body).

An objective of the present invention to provide a method and apparatus by which replaceable syringes can be more efficiently loaded into and unloaded from injectors.

Another objective of the present invention is to provide an injector with a replacement syringe and a method of replacing the syringe in the injector that provides a more efficient replacement of the syringes in the injector.

A further objective of the present invention is to provide a replaceable syringe and method of syringe replacement with which the replacement of the syringe can be achieved with simple motions by the operator or with rapid operation of injector unit mechanisms.

An additional objective of the present invention is to provide a replaceable syringe positive, rapid and reliable engagement of the syringe with locking structure that holds the syringe in the jacket, engagement of the plunger drive and plunger drive coupling, or connection of the injection tube to the outlet of the syringe.

Another objective of the present invention is to provide an injector and syringe arrangement that minimizes or eliminates the probability of spillage or leakage from the syringe nozzle flowing into the injector equipment, and otherwise enhancing the ability to maintain sterility and cleanliness of the equipment.

In one embodiment, the front end of the syringe is formed of a separate pressure restraining cap made of material that is separate from the front wall of the syringe and may be reusable. With the cooperating structure of the jacket and the syringe, restraining of the pressure jacket along the front and sides of the syringe is provided where the jacket allows for the replacement of the syringe from the front.

In another embodiment of the present invention, the threads are engageable in multiple but a limited number of angular positions. Additionally, other keys and key ways carried respectively by the unit and by the syringe limit the angular position in which the syringe may be inserted into the jacket to a unique predetermined angular orientation. Four key ways, such as slots or notches, spaced around the back, rearward or proximate edge of the syringe body, engage tabs on the unit at the rear end of the pressure jacket and in cooperation with the syringe umbrella cap and mating end of the pressure jacket.

Replacement of the syringe begins, in the embodiments of the invention, with unlocking the syringe at its front end from the front end of the pressure jacket, by rotating the syringe with respect to the jacket, and by disengaging the plunger drive from the syringe plunger, alternatively by transverse translational or rotational motion, simultaneous with and linked to the motion that disengages the syringe from the jacket. The unlocking of the syringe from the jacket occurs, for example, by loosening mating threads at the front of the syringe and jacket. The twisting of the syringe in the jacket is linked to motion that either translates transversely or rotates a coupling on the syringe plunger out of engagement with the plunger drive. The syringe is then removed from the jacket through the open front end of the jacket. This removal may take place without retraction of the plunger drive should the drive be advanced in the pressure jacket at the time of disengagement from the plunger coupling. The used syringe may also be removed without disconnection of the disposable injection tubing from the nozzle of the syringe.

In another aspect, the present invention also provides a disposable syringe that also provides a tight seal at the syringe nozzle and fluid delivery tubing connection.

These and other objectives of the present invention will be more readily apparent from the following detailed description of the drawings in which:

DETAILED DESCRIPTION OF THE INVENTION

As noted in the Background section, there is a need to more quickly load and unload disposable replacement syringes in injectors. A type of injector for the use of the present invention is described in U.S. Pat. No. 5,300,031; U.S. Pat. No. 5,451,211; and U.S. Pat. No. 5,658,261 which are incorporated by reference herein in their entirety.

Figure 1:
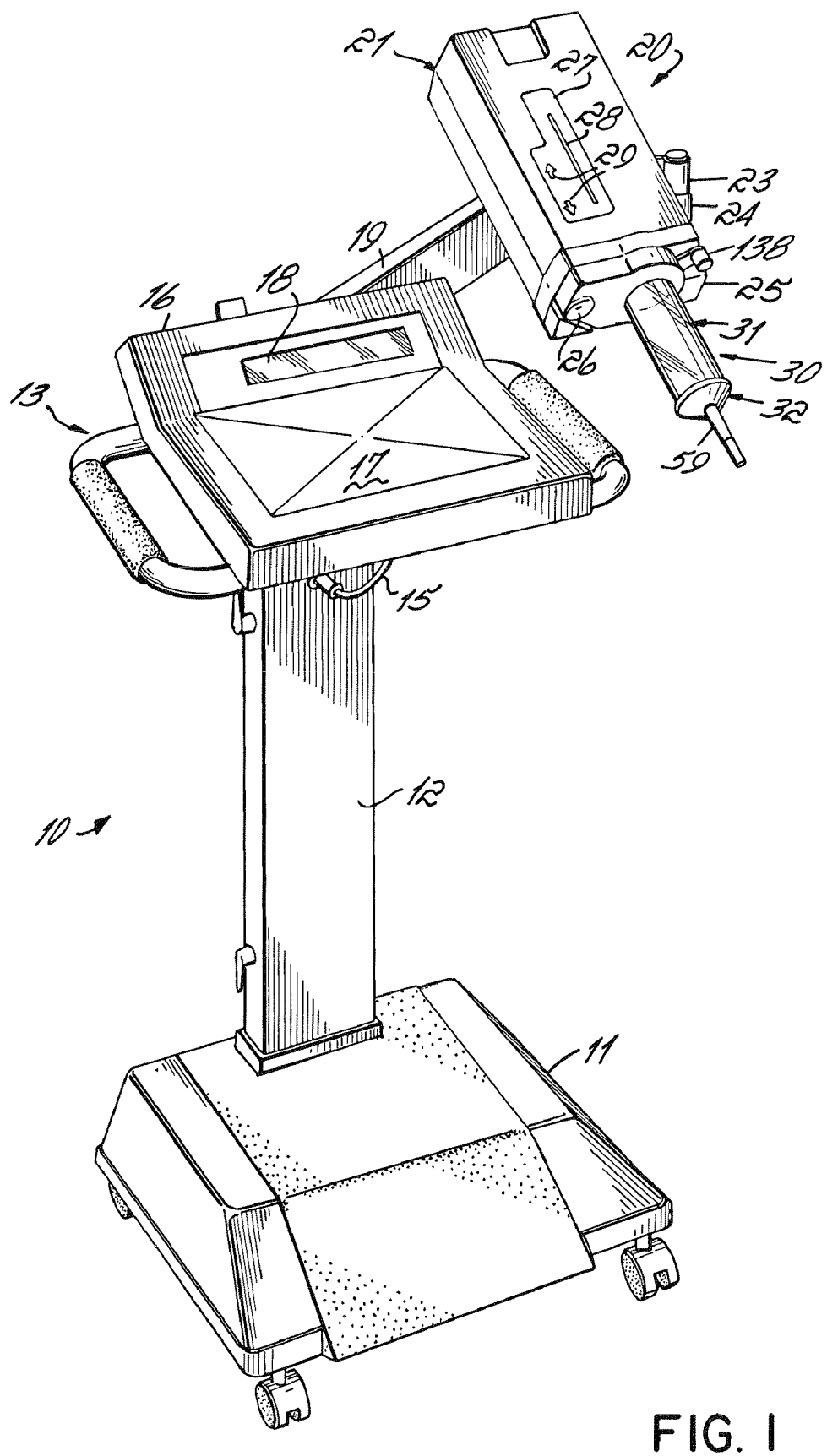
FIG. 1 is a perspective view of a form of an injector embodying principles of the present invention.

Briefly, an example of an injector 10 with use of the present invention is illustrated in FIG. 1. The injector 10 includes a wheeled base 11 to the top of which is rigidly supported a vertically adjustable upstanding support column 12. A control module platform 13 is supported at the top of the column 12. Electrical power is communicated from a power cord (not shown) through the base 11 and the upstanding support 12 and through a power lead 15 to a control module 16 rigidly supported to the platform 13. The control module 16 includes a programmable microprocessor (not shown) to which commands and programming codes are input through a keyboard 17 on the module 16. The module 16 is also provided with an operator display 18 to aid in interfacing the input commands and injector status with the operator. Attached to the platform 13 is an articulating adjustable arm 19. To the remote end of the arm 19 is adjustably supported the injection module unit 20.

The injection module unit 20 of the embodiments of FIG. 1 includes a housing 21 which contains the operating drive structure of the injector 10. The housing 21 has a support bracket 23 fixed thereto and adjustably pivotally supported to the remote end 24 of the articulating arm 19. The housing 21 has pivotally attached to the front thereof a door 25 at the front thereof which is pivotally connected to the housing 21 at a longitudinally extending pivot or hinge pin 26 (FIG. 2) rigidly supported on the housing 21 and extending forward from the front of the housing 21.

On the top of the housing 21 is an injector position and local control panel 27 having a position indicator scale 28 thereon, which displays the position of the injector drive to the operator. The panel 27 also includes a pair of forward and reverse drive direction control buttons 29, which are selectively actuatable to activate a drive within the housing 21 in either the forward or reverse directions.

Extending forward from the front of the door 25 is an injector syringe and pressure jacket assembly 30, the structure of which can be better understood with reference to FIGS. 2-5 below. The syringe and jacket assembly 30 includes a hard plastic pressure jacket 31, which may be of opaque or transparent material, a removable and replaceable disposable syringe 32, which may be of opaque, transparent or semi-transparent material, and related structure hereinafter described.

The syringe 32 is disposable, and includes walls which will withstand only moderate or low pressure. The walls are usually outwardly deformable under operating pressures, particularly pressures of 300 psi or more. Such higher pressures are necessary to overcome pressure drops through the injection tubing at higher flow rates, which are often desirable. The jacket 31 is made of a stronger transparent material that will withstand the operating pressures. When the syringe 32 is contained in the jacket 31, it is surrounded by the jacket 31 and supported by the jacket 31 against expansion caused by the fluid pressure within as the syringe 32 expands against the jacket wall.

Figure 2:
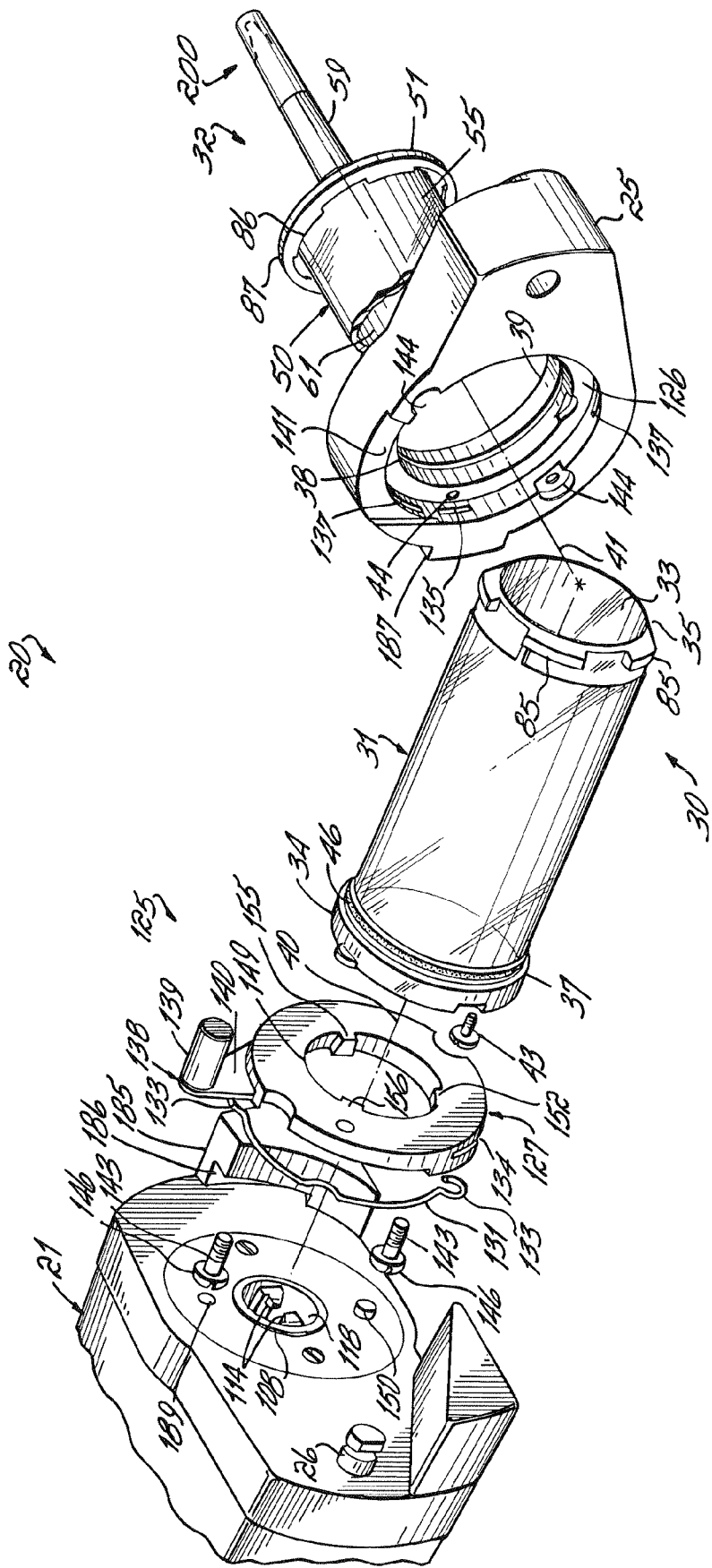
FIG. 2 is an exploded perspective view of a portion of an embodiment of the injector of FIG. 1.

The pressure jacket 31 has a generally cylindrical inner bore 33 extending therethrough from a proximate end 34 adjacent the door 25 to a remote end 35 of the pressure jacket 31 toward the front of the unit 20. The bore 33 is dimensioned so as to receive through the remote end 35 the disposable syringe 32 and to support the syringe against expansion from fluid pressure within such fluid pressure may range to more than a thousand psi. The pressure jacket 31 has an annular flange 37 extending outwardly around the proximate end 34. The flange 37 is integrally formed with the jacket cylinder and is shaped to conform to an annular recess 38 surrounding a circular hole 39 in the door 25 to which the jacket 31 may be assembled by insertion from the rear. The hole or opening 39 in the door 25 and the cylindrical bore 33 of the jacket 31 are concentric with a longitudinal axis 40 on which also lies an axis 41 of the syringe 32 when the syringe 32 is positioned in the bore 33 of the jacket 31. The jacket 31 is firmly and rigidly attached to the door 25 with a pair of screws 43, only one of which is shown, which are threaded into a pair of holes 44 in the back of the door 25 (FIG. 2). An O-ring seal 46 surrounds the flange 37 of the jacket 31 in the recess 38 of the door 25.

The syringe 32 includes a syringe case 50 formed of a single piece of molded plastic material, a pressure cap 51 and a plunger 54 (FIGS. 3A, 4A-5). The syringe case 50 includes a cylindrical syringe body 55 having an open proximate end 56 and a remote end 58 to which is integrally formed a conical front wall 57. The front wall 57 is truncated at its forward end, to which is integrally formed an elongated neck 59 extending from the wall 57 at the center thereof. The neck 59 of the syringe case 50 has an orifice 60 (FIG. 3A) in its remote or distal end which communicates with an internal syringe cavity 61 formed of the interior of neck 59, the interior of conical front wall 57 and the interior of cylindrical body 55 of the case 50 of the syringe 32. The rear end of the cavity 61 is further defined by a forward facing conical surface 64 of the plunger 54. The conical surface 64 is of a slope which conforms to the slope of the interior of the conical front wall 57. The plunger 54 is slidable within the body 55 of the syringe case 50 such that the cavity 61 is of variable volume.

Figure 3A:
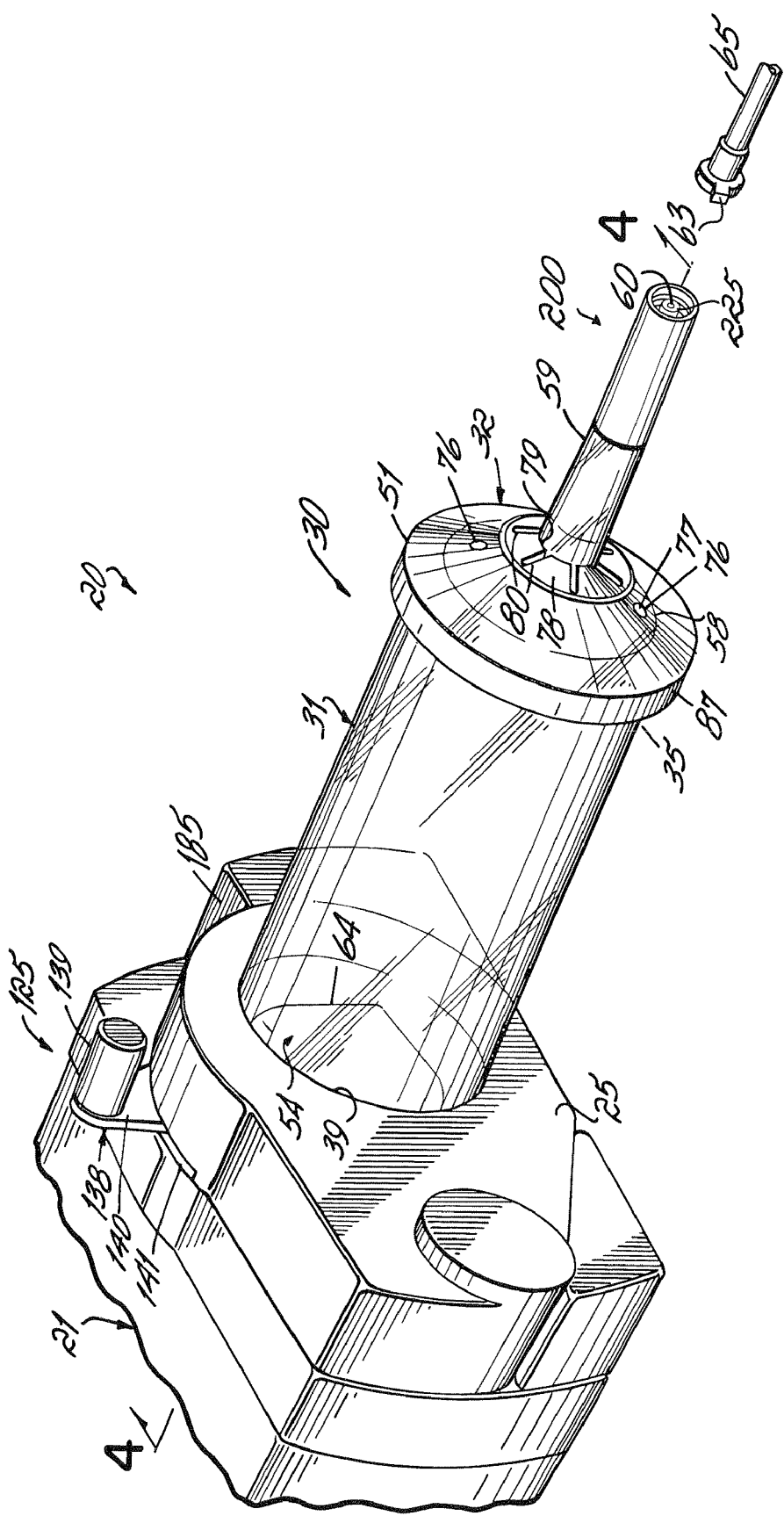
FIG. 3A is a perspective view of a portion of the injector of FIG. 2.
Figure 3B:
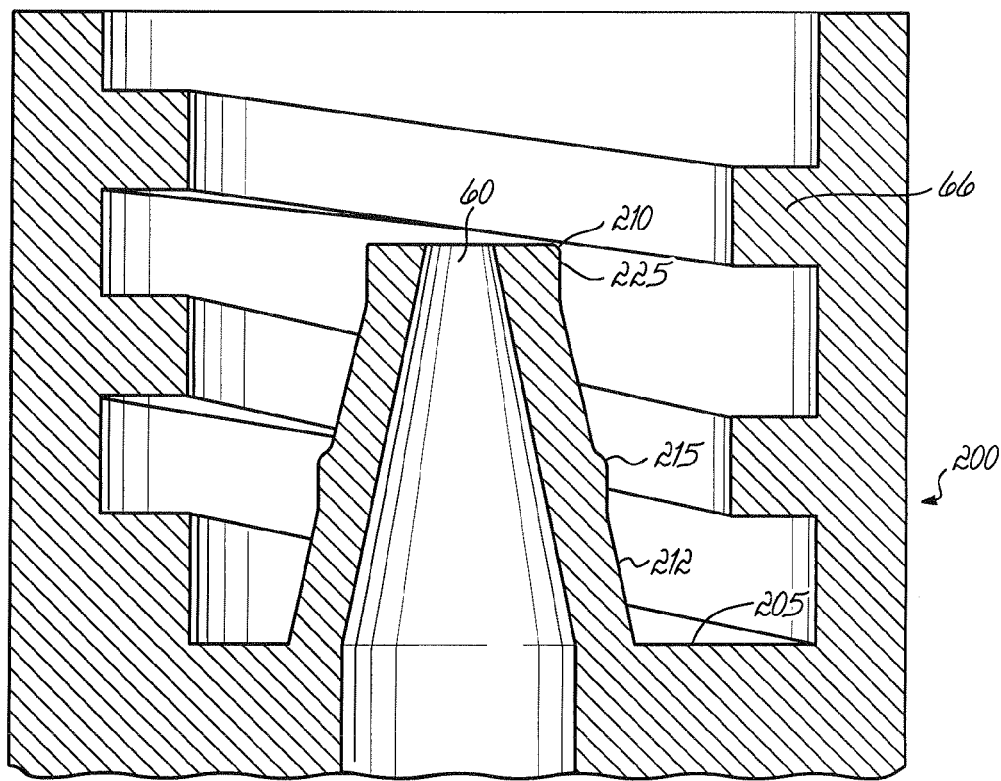
FIG. 3B is a cross-sectional view of the connector tip of the syringe within a receiving end of fluid delivery tubing.
Figure 3C:
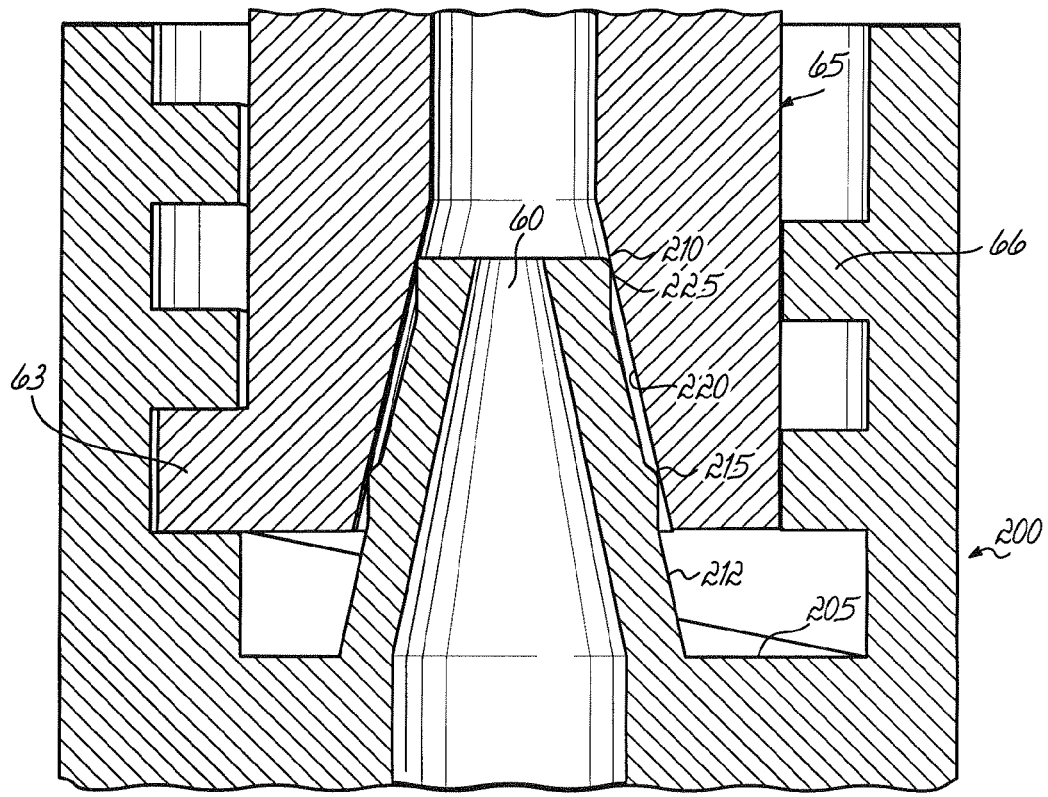
FIG. 3C is a cross-sectional view of an end of a fluid delivery tube installed in the connector tip of the syringe.

In one embodiment best seen in FIGS. 3B and 3C, near the front or remote or distal end of the neck 59 of the syringe case 50, a tubing connector 200 has an internally threaded section 66 configured to mate with thread 63 on the exterior of tubing 65. In another embodiment, two or more threads may be on the exterior tubing 65.

The tube connector 200, also known as a Luer tip or Luer connection, on distal, or remote, end of neck 59 of syringe case 50 has a specific structure which enables it to connect to a fluid delivery tube 65 (FIG. 3A). As illustrated in FIG. 3B, the connector 200 has about a six-degree taper 212 extending from the proximal end 205 to the distal end 210 of the connector 200. The taper 212 includes at least one ridge 215, or knurl along the outer surface of the taper 212 that acts as a sealing ring and is in contact with the inner surface 220 of the connecting end of tube 65.

In another embodiment, the taper 212 includes at least two ridges or knurls 215, 225 along the outer surface of taper 212. These sealing rings reduce, eliminate, or prevent leakage between the connector 200 and the connector of the delivery fluid tube 235, and also facilitate connection and removal of tubing. One of the ridges 225 is located at the distal end 210 of the connector 200. The second ridge 215 may be positioned at any location along the taper 212 such as midway between the proximal end 205 and distal end 210 of the connector 200.

The functionality of ridges or knurls 215 and 225 is best seen in FIG. 3C. When tubing 65 is connected to connector 200, only the ridges 215, 225, or sealing rings, of the connector 200, are in contact with the inner surface 220 of the tube 65, thus reducing the surface area contact of the connector 200. This reduction in surface area increases contact pressure between the connector 200 and the tube 65. The increased contact pressure provides a better seal at the connector 200/ tube 65 connection. Furthermore, the reduction in surface area reduces the friction between the tubing 65 and connector 200, such that the tubing is inserted and removed with a reduced torque for a given contact pressure than would be the case in the prior art. The ridges or knurls 215 and 225 thus achieve two benefits of increasing contact pressure and improving sealing, and reducing friction to make insertion and removal easier.

Figure 4A:
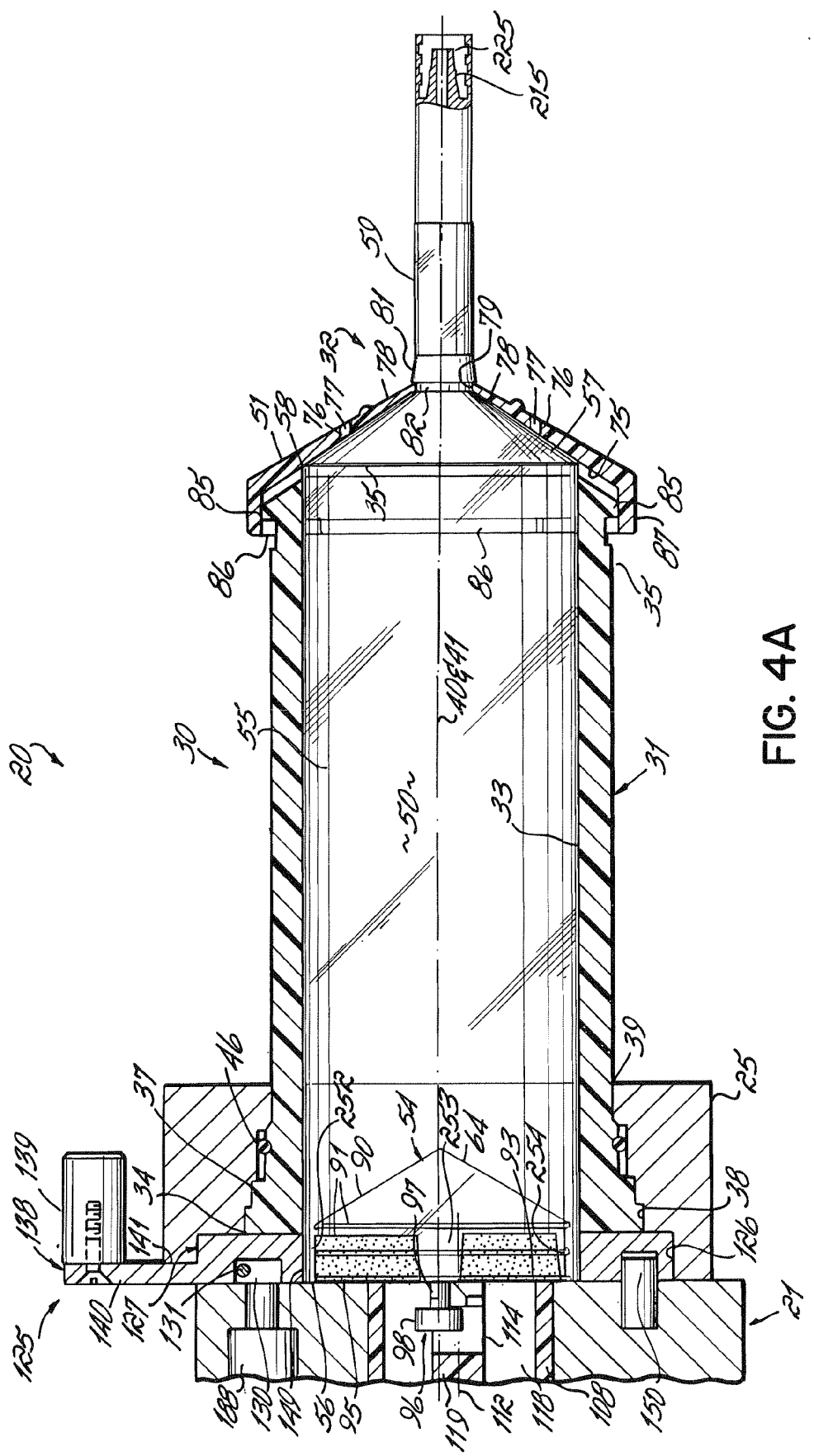
FIG. 4A is a cross-sectional view along lines 4-4 of FIG. 3A illustrating a replaceable syringe unlocked from the housing after insertion into the pressure jacket and prior to locking thereto, or after unlocking from the pressure jacket and prior to removal therefrom.
Figure 4B:
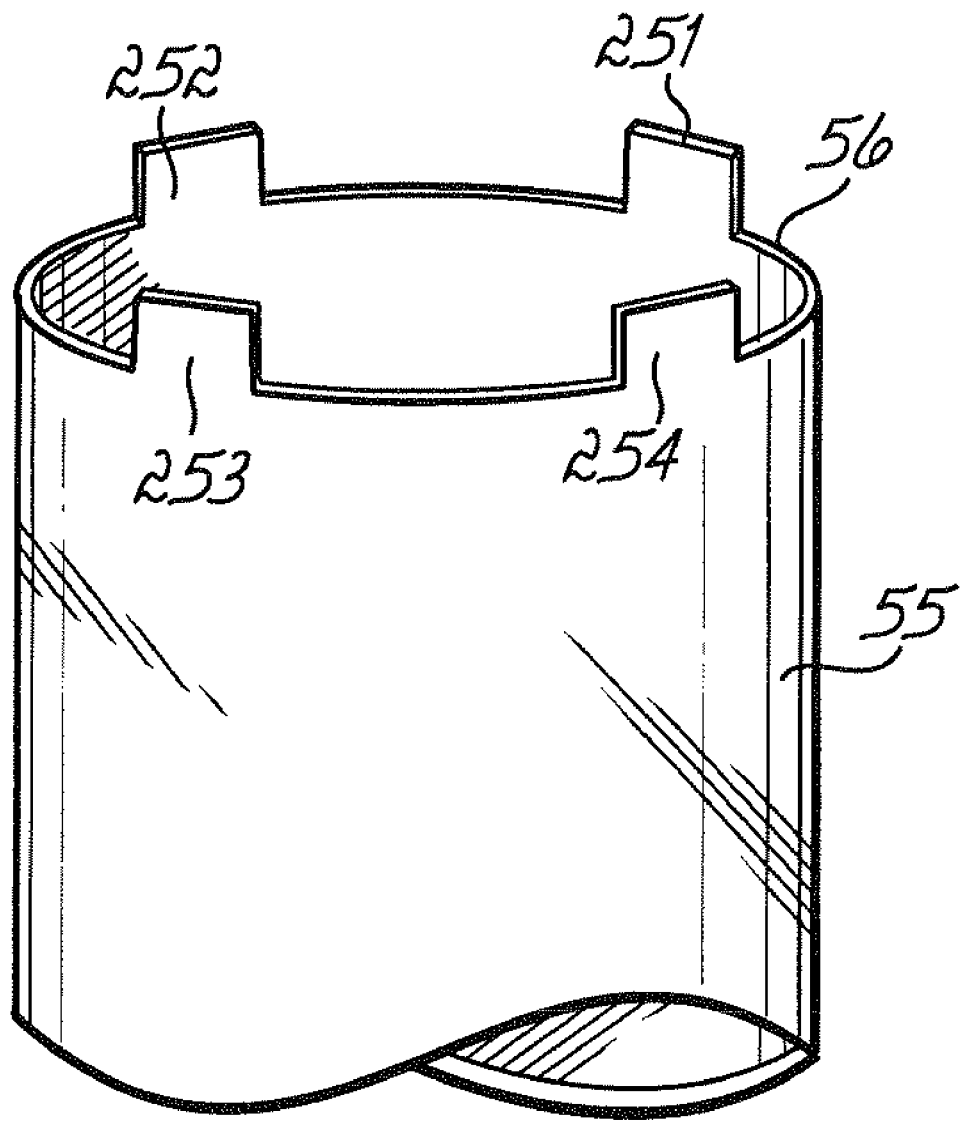
FIG. 4B is a perspective view of the notched proximal end of the syringe.

Turning more specifically to FIG. 4A, it may be seen that the cap 51 is generally conical in shape and has an inner rearward surface 75, which conforms to the front surface of the conical wall 57 of the case 50 of the syringe 32. In certain embodiments, the rearward conical surface 75 of the cap 51 may be bonded to the front surface of the conical wall 57 of the case 50 of the syringe 32, or it may be formed integrally therewith, molded from the same plastic material as the case 50 of the syringe 32. In the illustrated embodiment, the cap 51 is separate from the syringe body portion 55 and has a pair of holes or detents 76 into which fit a pair of projections 77 extending forward from and formed integrally on the outer surface of the conical wall 57 of the case 50 of the syringe 32. The cooperation of the pins or projections 77 with the holes or detents 76 prevent the cap 51 from rotating with respect to the syringe case 50 when the cap 51 is mounted on the syringe 32.

To hold the cap 51 against the conical wall 57 of the case 50 of the syringe 32, six resilient tabs 78 are formed about a central inner hole 79 of the cap 51. The tabs 78 are separated by six equally spaced radial slots 80 (FIG. 3A). The hole 79 in the cap 51 is equal to or only slightly greater in size than the circular forward end of the conical wall 57 of the case 50 of the syringe 32. The neck 59 of the syringe 32 has an enlarged straight section 81 slightly greater in diameter than the hole 79 in the cap 51 and also greater in diameter than the forward end of the conical wall 57 of the case 50, thereby forming a groove 82 at the juncture of the straight neck portion 81 with the conical wall 57 so that the tips of the tabs 78, which are sufficiently resilient to slide over the enlarged neck portion 81 as the cap 51 is inserted on the case 50 of the syringe 32 with the hole 79 surrounding the neck 59 to snap fit into the groove 82.

Figure 5:
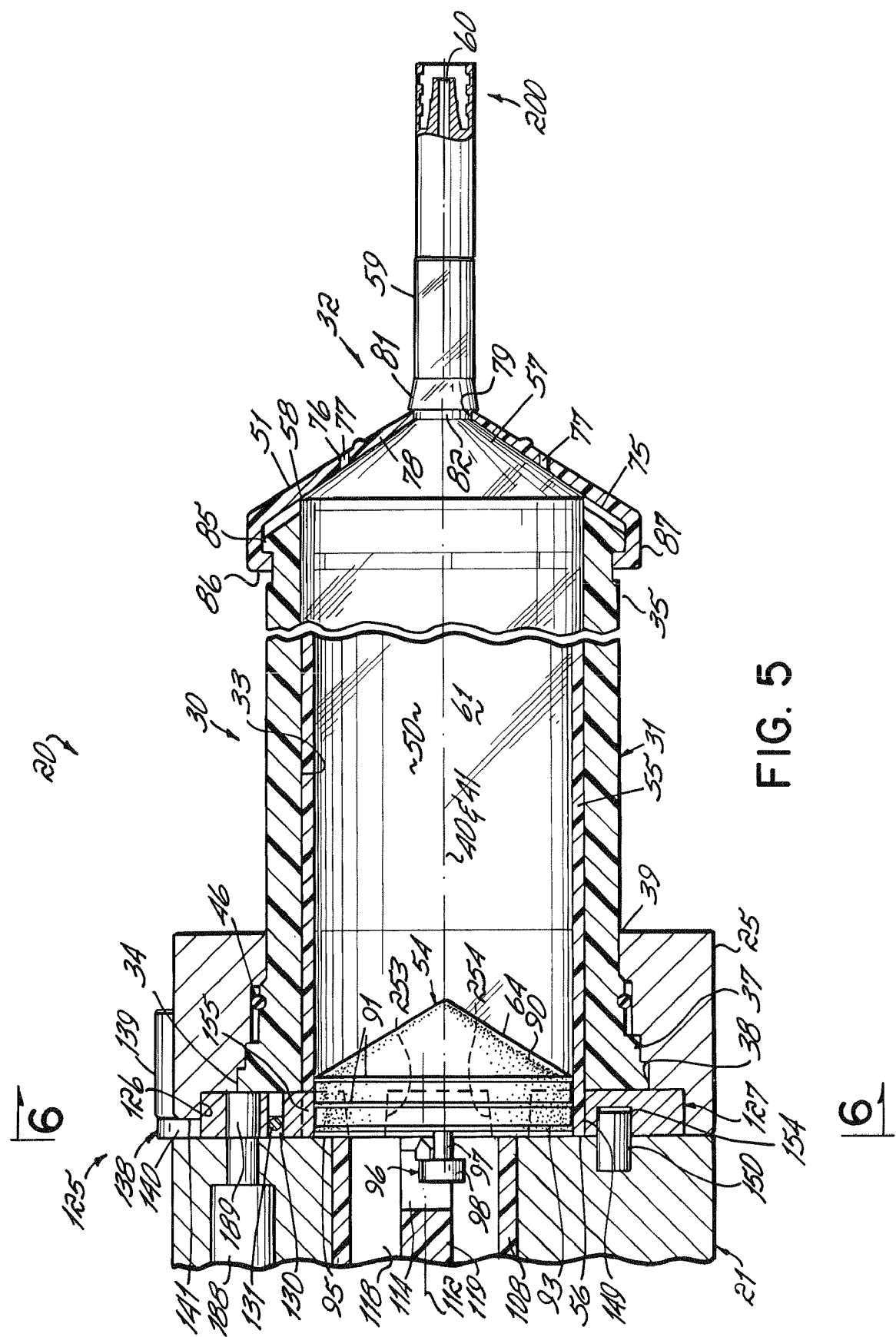
FIG. 5 is a cross-sectional view similar to FIG. 4 but illustrating the syringe locked to the structure carried by the housing.

Referring to FIGS. 2 and 4A, the syringe 32 includes structure that is configured to lock the syringe 32 to the front end of the jacket 31 by cooperating with mating structure on the jacket 31. The jacket 31 has, spaced around the circumference thereof near the remote or front end 35 of the jacket 31, four equally spaced outwardly projecting thread sections 85. These thread sections 85 are slightly less than 45° in extension around the circumference of the jacket 31 and are spaced apart with gaps of slightly greater than 45°. The cap 51 has a cylindrical rim 87 in which are formed four similarly sized and spaced mating thread sections 86. The thread sections 86 project inwardly toward the jacket 31 when the syringe 32 is positioned in the jacket 31. As such, when the syringe 32, with the cap 51 assembled to it is inserted into the jacket 31, the threads 86 of the cap 51 pass through the spaces between the threads 85 on the jacket 31 to a point behind the threads 85. When so inserted, the syringe assembly 32 with the cap 51 may be twisted clockwise 45° to tighten and thereby secure the cap 51 to the jacket 31 by engagement between the threads 85 and 86 as shown in FIG. 5, to thereby lock the syringe in the bore 33.

The plunger 54 of the syringe 32 is molded of an elastomeric material. Preferably, the plunger 54 includes two portions molded of different materials and bonded together. These portions include a forward more flexible portion 90 in which is formed the forward conical surface 34. This forward portion 90 has a pair of outwardly extending rings 91 formed in the periphery thereof to make sealing engagement with the inside of the wall of the cylindrical body 55 of the syringe case 50. The rearward portion of the piston 54 is a flat circular surface to which is bonded the flat circular forward surface of a more rigid rear portion 93 of the piston 54. The rear rigid portion 93 of the piston 54 is molded of a harder stronger plastic material and has a rearward facing circular surface 95 having a rearward extending coupling 96 integrally formed thereon at its center. The coupling 96 includes a rearwardly extending cylindrical shaft 97 on the axis 41 of the syringe 32 and a larger symmetrical cylindrical button 98 integrally formed at the rear end of the cylindrical shaft 97.

At the forward end of the carriage 108 is supported a pair of hooked jaws 114 which are pivotally mounted at their rearward ends by a pair of pivot pins 115 to the carriage 108. The jaws 114 are biased toward the axis 112 by a pair of balls 116a and 116b of resilient material positioned between the outside of the jaws 114 and an inner cylindrical wall 117 of a recess 118 formed in the forward end of the carriage 108. The balls 116a, 116b are partially captured in depressions in the outer surfaces of the jaws 114. The balls 116a, 116b bias the jaws toward their innermost position toward the axis 112. The innermost position of the jaws is determined by a spacing block 119 on the axis 112 of the carriage 108 at the center of the cavity 118.

When a syringe 32 is locked in the jacket 31 with its axis 41 and the axis 40 of the jacket 31 may be in alignment with the axis 112 of the shaft 105, the plunger 54 may be located in the cylindrical body 55 of the syringe case 50 in a position forward of the remote end 56. Preferably, however, the jaws 114 are displaced to the side of axis 112 of the shaft 105 so that as the jaws 114 and coupling tip 98 are in their disengagement position, maximum clearance is provided so that the syringe 32 may be inserted into the jacket 31 without the sterile internal walls of the syringe 31 touching the components of the drive, as illustrated in the figures.

Figure 11:
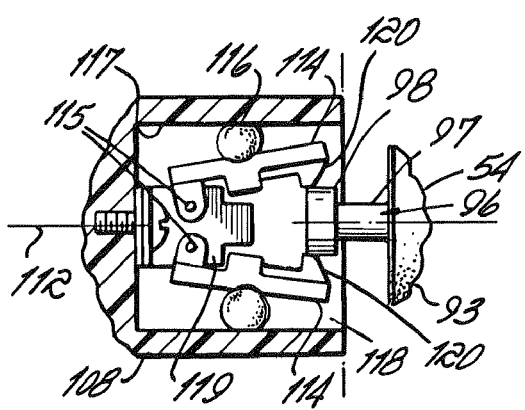
FIG. 11 is a view of a portion of FIG. 10 illustrating the plunger drive longitudinally moving into engagement with the plunger coupling.
Figure 12:
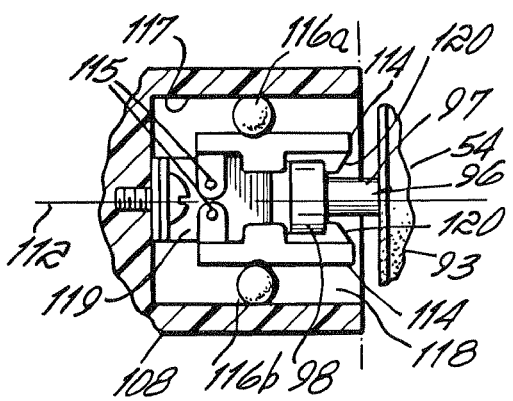
FIG. 12 is a view of a portion of FIG. 10 illustrating the plunger drive in engagement with the plunger coupling.

In the engaging position, the jaws 114 are in alignment with the coupling 98 on the axes 40 and 41 of the jacket 32 and syringe 32. In such a situation, the jaws 114 may be in a retracted position at the center of the opening 39 of the door 25 adjacent to the proximate end 34 of the jacket 31, and out of engagement with the coupling 96 on the plunger 54. From this position, operation of the motor 101 rotates the shaft 105 and drives the carriage 108 forwardly to move the jaws 114 toward and into engagement with the coupling 96 on the plunger 54. This engagement takes place as shown in FIG. 11 where a pair of tapered cam surfaces 120 at the forward interface of the tips of the jaws 114 engage the enlarged portion or button 98 of the coupling 96 to expand the jaws, as shown in FIG. 11, to snap around the button 98 of the coupling 96 to form a driving engagement between the drive assembly 100 and the coupling 96 of the plunger 54 as shown in FIG. 12. Once so engaged, any forward or reverse movement of the carriage 108 under the power of the motor 101 will cause the plunger 54 to be driven either forwardly or backwardly in the syringe body 55.

Disengagement of the jaws 114 from the coupling 96 can thereafter be achieved by translational movement between the coupling 96 and the jaws 114 between a disengaged position as shown in FIG. 4A and an engaged position as shown in FIG. 5. When the plunger coupling 96 and the jaws 114 are disengaged, the syringe 32 can be replaced without the need to retract the carriage 108 of the drive 100. This allows for rapid replacement of the syringe 32. Preferably, the jaws 114 are either fully retracted toward the housing 21 where engagement by translation of the coupling 96 will occur, or the jaws 114 are sufficiently within the jacket prior to replacement of the syringe so that the coupling 96 of the replacement syringe 32 will not contact the jaws 114 except as the drive 100 is advanced.

If sterility is not a problem, the most time saving approach would be to insert the syringe 32 into the jacket 31 with its plunger all the way forward and the drive fully advanced so that, when the syringe is translated toward the jaws 114, engagement will immediately occur and the plunger can be immediately retracted to fill the syringe.

When a syringe 32 is inserted into the jacket 31 when the plunger 54 is at its rearmost position toward the proximate end 56 of the syringe body 55, the coupling 96 is in a position adjacent the proximate end 56 of the syringe body 55 and projecting rearwardly therebeyond. When in such a position, engagement between the jaws 114 and the coupling 96 is brought about by translational movement between the position shown in FIG. 4A and that shown in FIG. 5. In the unlocked or disengaged position shown in FIG. 4A, the axes 40 and 41 of the jacket 31 and the syringe 32, respectively, as well as the center of the opening 39 of the door 25, lie spaced from and parallel to the axis 112 of the shaft 105 as shown in FIG. 4A. In the locked or engaged position, the axis 112 of the shaft 105 is slightly eccentric relative to the axes 40 and 41 of the jacket 31 and syringe 32, respectively, as shown in FIG. 5. This translational movement, the engagement and disengagement between the coupling 96 and the jaws 114 and the 45E rotational movement which secures the cap 51 to the pressure jacket 31 by engagement of the threads 85 and 86 are brought about by operation of a translating and locking mechanism 125, which is best understood by reference to FIGS. 2-9.

The translating and locking mechanism 125 includes a syringe engaging device, or a cam and locking ring 127, which is rotatably retained in a circular recess 126 in the back of the door 25. The ring 127 has a generally semi-circular groove 130 in the back surface thereof for receiving a spring wire retaining clip 131 having a pair of looped ends 133 which extend through a pair of slots 134 in the rim of the ring 127 and into a selected one of three pair of diametrically opposed notches 135, 136 and 137 in the inner wall of the rim of the recess 126 in the door 25. The three pair of notches 135, 136 and 137 represent three positions of the translating and locking mechanism 125 which are the locked, unlocked and release positions, respectively. The locked position of the mechanism 125 in which the loops 133 of the ring 131 are in the notches 135, is that illustrated in FIGS. 5-7 and 10. The unlocked position, in which the loops 133 of the ring 131 are in the notches 136, is that illustrated in FIGS. 2-4 and 8. The release position, in which the loops 135 of the clip 133 are in notches 137, is that illustrated in FIG. 9. The ring 127 is moved among these three positions by a manually accessible handle 138 in the form of a cylindrical knob 139 rotatably attached to a lever arm 140 formed integrally and extending radially from the ring 127 through a slot 141 in the door 25 (FIG. 1). The ring 127 is retained in the recess 126 by a pair of screws 143 which thread into countersunk holes 144 at the periphery of the recess 126 in the back of the door 25. These screws 143 have enlarged heads 146, which, when seated in the holes 144, overlie the edge of the ring 127, thereby securing it for rotatable movement within the recess 126.

Figure 6:
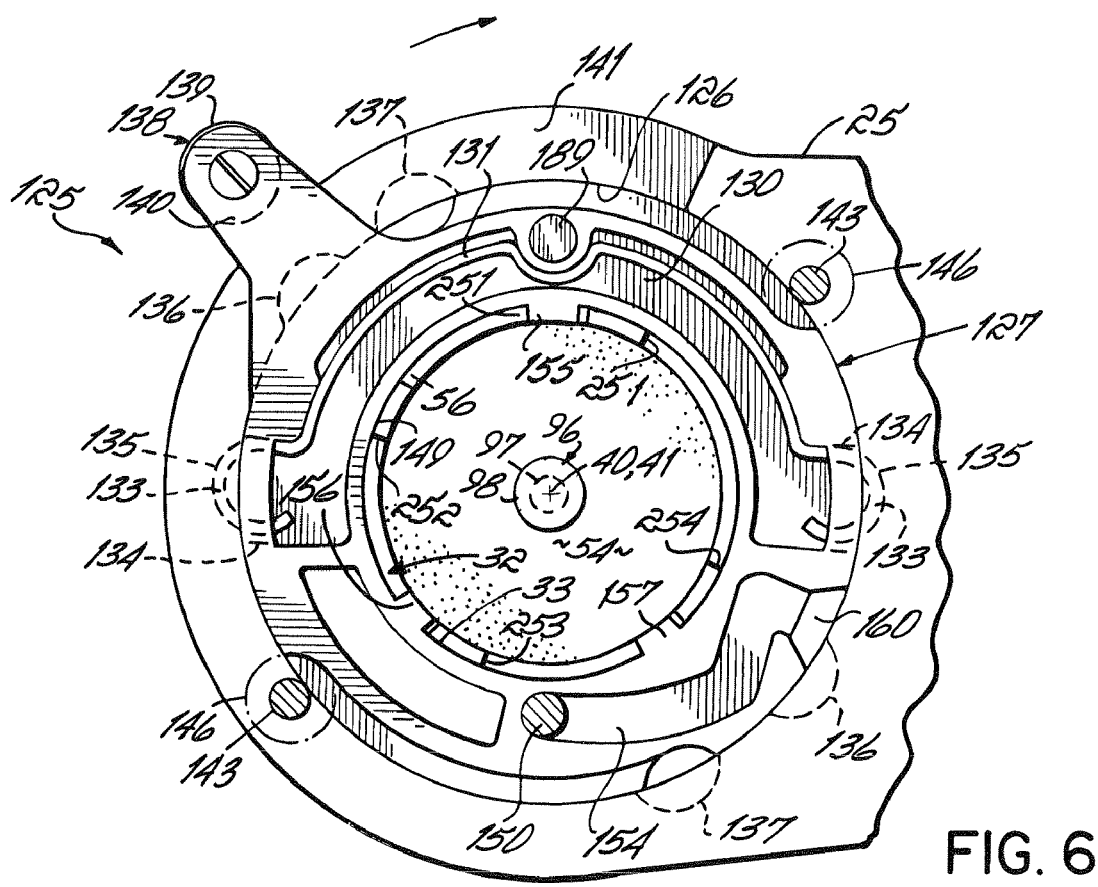
FIG. 6 is a cross-sectional view along the line 6-6 of FIG. 5.

As shown in FIGS. 2 and 6, the ring 127, or rotatable cam, has an inner periphery 149 which is larger than the circumference of the body 55 of the syringe case 50. Accordingly, when the syringe 32 is inserted in the jacket 31, the proximate end 56 of the syringe case 50 extends through and is surrounded by the inner periphery 149 of the ring 127 (rotating cam). A key, or keyway, engaging structure, in one embodiment, is in the form of four projections 251, 252, 253 and 254 (FIGS. 4A, 4B) provided in the edge of the proximal end 56 of the body 55 of the syringe case 50. The four projections 251-254 are equally spaced.

Formed integrally of the ring 127 and projecting inwardly from the inner periphery 149 thereof are three tabs or keys 155, 156 and 157. The tabs 155-157 are unequally spaced around inner periphery 149, such that the tabs or keys 155, 156 and 157 fit between the respective projections 251-254 in the proximate end 56 of the body 55 of the syringe case 50, so as to rotate the syringe 32 as the mechanism 125 is rotated through actuation of the handle 138, or alternatively, to rotate the mechanism 125 as the syringe 32 is rotated at its end.

Any one of the spaces between projections 251-254 may be engaged with the keys or tabs 155-157 of ring 127. This allows the syringe 32 to be attached to the door 25 and pressure jacket 21 assembly in any one of four orientations as dictated by the four thread sections 85 of the cap 51. The syringe may thus be retrofitted to the faceplates of the injectors described in U.S. Pat. No. 5,300,031; U.S. Pat. No. 5,451,211; and U.S. Pat. No. 5,658,261, incorporated herein in their entirety, since the tabs 155-157 in the ring 127 are compatibly positioned as compared to the injectors of these three patents.

The rotation of the mechanism 125 from the unlocked position to the locked position rotates the syringe 32 in the jacket 31 and rotates the cap such that its threads move from an unlocked position as shown in FIG. 4A to the locked position of FIG. 5, to secure the cap to the jacket 31 by the engagement and tightening of the threads 85 and 86.

The translational movement of the axes 40 and 41 with respect to the axis 112 is achieved by a fixed cylindrical cam follower or pin 150 which projects outwardly from the fixed housing portion 22 behind the ring 127 and into a cam slot 154 formed therein. The slot 154 is shaped so that the axes 40 and 41 which remain fixed with respect to the ring 127, along with the door 25, the jacket 31, the syringe 32 and all of the structure mutually carried thereby, are moved in relation to the axis 112 of the shaft 105 and the other structure mutually carried by the housing 22, as the mechanism 125 is rotated. These axes move toward and away from each other in accordance with the shape of the slot 154 determined by the radial distance from the point along the slot 154 where it engages the pin 150 to the axes 40 and 41.

Figure 7:
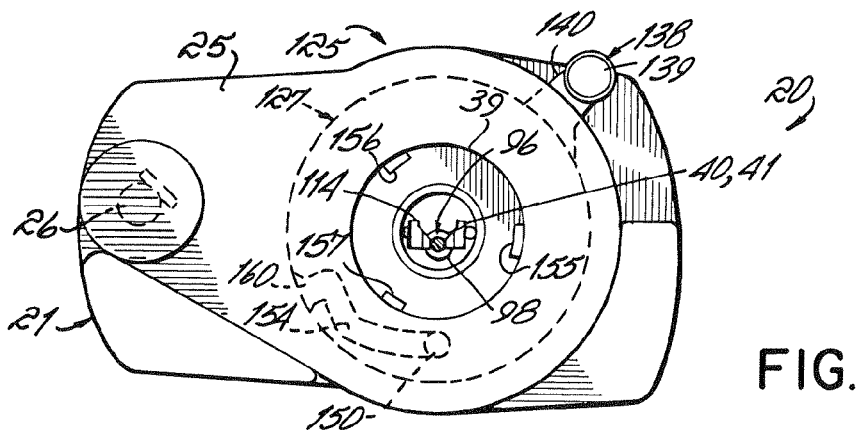
FIG. 7 is an elevational diagrammatic illustration of the injector of FIG. 1 with the pressure jacket and syringe removed, and showing the syringe locking structure in the locked position such as in FIGS. 5 and 6.
Figure 8:
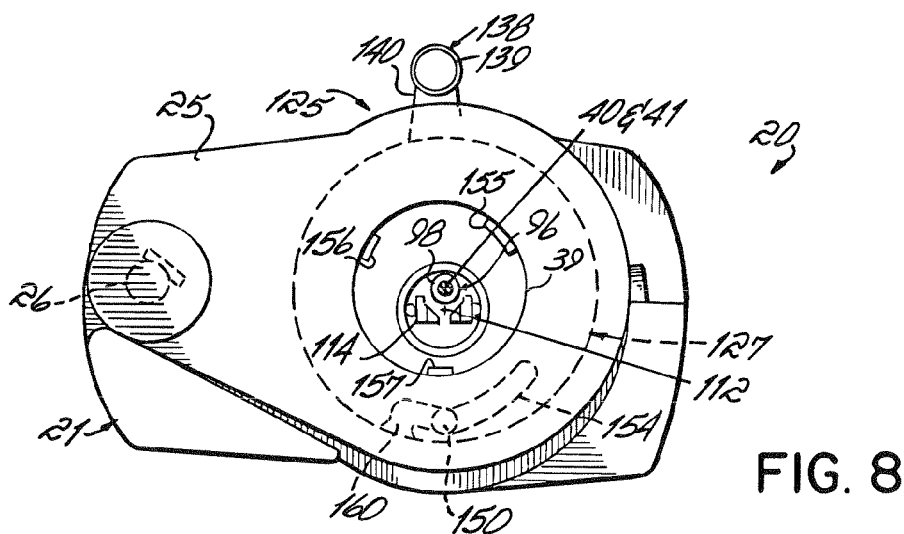
FIG. 8 is an elevational diagrammatic view similar to FIG. 7 illustrating the syringe locking structure in the unlocked position such as in FIGS. 2-4.

The cam slot 154 in the ring 127 is shaped such that, when the mechanism 125 is in the locked position as shown, for example, in FIGS. 6 and 7, the distance between the pin 150 and the axes 40 and 41 is at a minimum and the axis 112 coincides with the axes 40 and 41. This is illustrated in FIGS. 5 and 7 wherein the coupling 96 is shown positioned between the jaws 114 and in mutual engagement therewith. When the mechanism 125 is in the unlocked position, with the loops 133 of clip 131 in the notches 136 (FIG. 6) of the recess 126, the pin 150 lies in the slot 154 in the position shown in FIG. 8, which is farther displaced from the axes 40 and 41 than in the position of FIGS. 6 and 7, so that the coupling 96 is translated to a position outside of the center line of the jaws 114, as shown in FIG. 8 and further illustrated in FIG. 4A.

Figure 9:
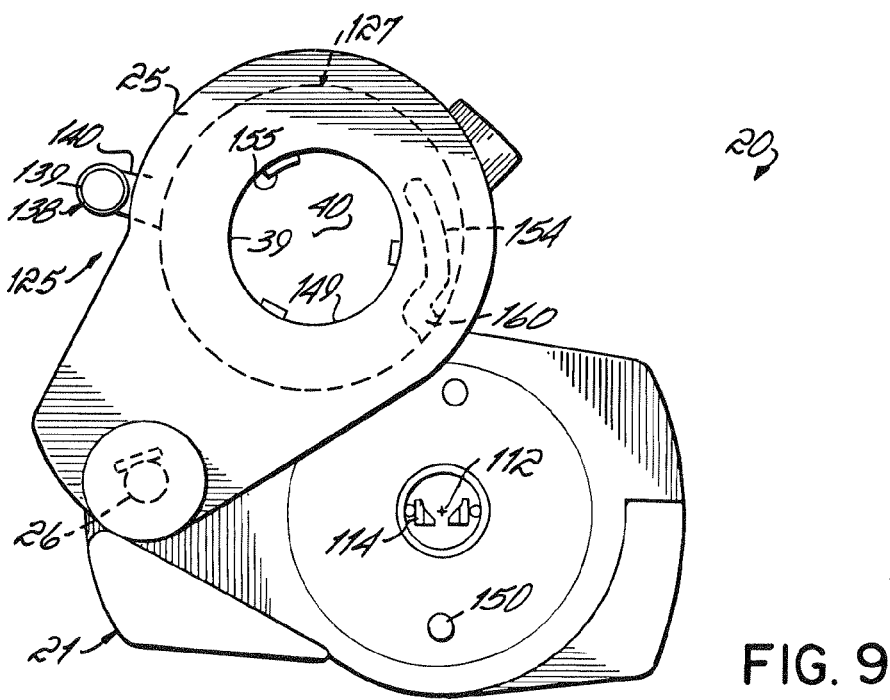
FIG. 9 is an elevational diagrammatic view similar to FIG. 7 illustrating the locking mechanism in the housing door release position.
Figure 10:
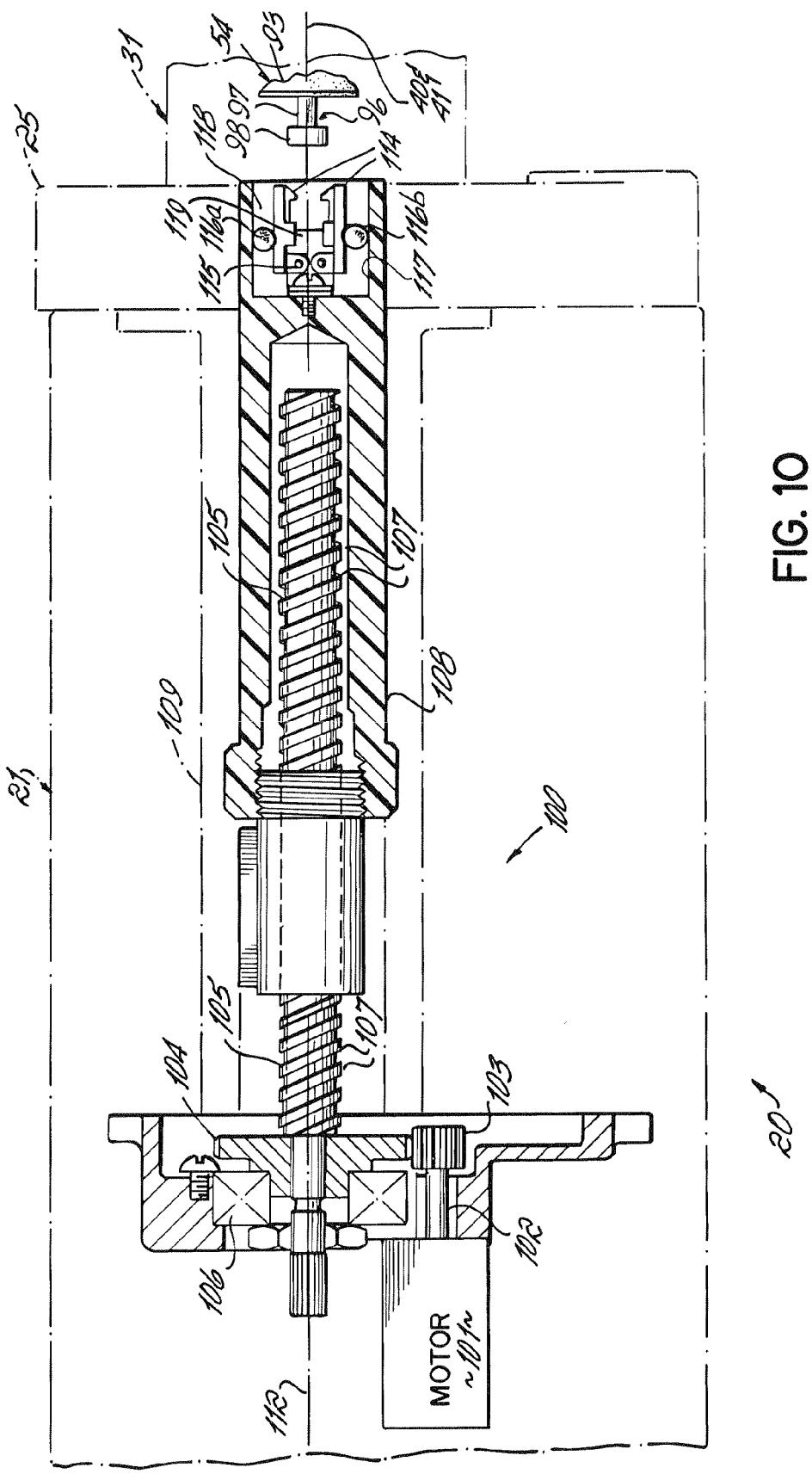
FIG. 10 is a cross-sectional view through the housing of the injector taken along lines 10-10 of FIG. 1 with the plunger drive disengaged from the syringe plunger coupling.

In the release position, as shown in FIG. 9, the pin 150 is positioned at the open end 160 of the cam surface of the slot 154 so that the door 25 can be rotated upwardly about the hinge pin 26, as shown in FIG. 9, to open the space behind the door 25 for access thereto. This position may be used for cleaning the area behind the door 25 which is sometimes necessary because of possible leakage of fluid from the cavity 61 into the space behind the plunger 54. This can possibly occur because the fluid within the cavity 61, when being injected by forward advancement of the plunger 54, may be of relatively high pressure in the range, usually over 200 psi. For applications such as the injection of contrasting fluid for CT scanning, pressure may typically be in the range of from 25 to 300 psi, while in some injection applications the pressure may range to 1200 psi or higher.

Leakage rearwardly along the exterior of the neck 59 of the syringe 32 can cause fluid to flow between the body portion 55 of the syringe 32 and the jacket 31. For this reason, the cap 51 is caused to fit snugly against the forward surface of the conical portion 57 of the syringe 32 at least sufficiently to restrict the flow of this leaking fluid onto the neck 59. This is assisted by the configuration of the cap 51 at the rim 87 thereof so as to divert away from the space between the syringe 32 and jacket 31 fluid which might leak from the nozzle.

As seen in FIG. 2, the front of the housing 21 has formed thereon a door stop 185 having a slot 186 formed therein for receiving a lug 187 of the door 25, to restrain the door 25 against forward force exerted by the drive 100. As seen in FIGS. 4A and 5, behind the front of the housing 21 adjacent the stop 185 is a magnetic sensor 188, which is responsive to the presence of a magnet 189 in the ring 127. The sensor 188 generates a signal to the control module 16 to activate the drive 100 only when the mechanism 125 is in its locked position.

The locking structure between the syringe 32 and the pressure jacket 31 should provide for retention of the syringe 32 in the jacket 31 against the force of the fluid pressure in the cavity 61 or axial force otherwise exerted on the plunger 54 by the drive 100. This locking of the syringe 32 to the jacket 31 is preferably achieved, as shown in FIG. 5, by structure at or near the forward wall 57 of the syringe case 50.

The invention has been described in the context of its preferred embodiments. It will be appreciated by those skilled in the art that variations and alternatives to the embodiments described may be employed without departing from the principles of the present invention. Accordingly, this patent is not intended to be limited except by the scope of the following claims.

What is claimed is:

1. A syringe comprising:
 a syringe case comprising:
  a proximal end and an opposing remote end;
  a discharge neck located at the remote end of the syringe case; and
  tubing connector located at a remote end of the discharge neck, the tubing connector comprising:
   a taper comprising a proximal end, an opposing distal end, an annular first ridge disposed at the distal end of the taper about a peripheral circumference of the taper and spaced from a proximal end of the taper, and an annular second ridge disposed between said proximal and distal ends about a peripheral circumference of the taper; and
   an internal threaded section disposed about the taper at least in the portion of said taper including said annular first ridge and annular second ridge, wherein the internal threaded section is substantially immobile relative to the taper; and
 a plunger disposed within an internal cavity of the syringe case.

2. The syringe of claim 1, wherein the taper is at least a six degree taper.

3. The syringe of claim 1, further comprising:
 a pressure cap connected to a front wall of the syringe case.

4. The syringe of claim 1, wherein the syringe case is formed of molded plastic material.

5. The syringe of claim 1, further comprising:
 a medical fluid disposed within an internal syringe cavity of the syringe case.

6. The syringe of claim 5, wherein the medical fluid is contrast media.

7. An injector assembly for injecting medical fluid into a patient, comprising:
 an electrically powered injector; and
 a syringe mounted to the injector, the syringe comprising:
  a unitary, single piece syringe case comprising:
   a proximal end and an opposing remote end;

a discharge neck located at the remote end of the syringe case; and tubing connector located at a remote end of the discharge neck, the tubing connector comprising:
- a taper comprising a proximal end, an opposing distal end, an annular first ridge disposed at the distal end of the taper about a peripheral circumference of the taper and spaced from a proximal end of the taper, and an annular second ridge disposed about a peripheral circumference of the taper; and
- an internal threaded section disposed about the taper at least in the portion of said taper including said annular first ridge and said annular second ridge, wherein the internal threaded section is substantially immobile relative to the taper; and a plunger disposed within an internal cavity of the syringe case.

8. The injector assembly of claim 7, wherein the second ridge is disposed between the proximal end and the distal end of the taper.

9. The injector assembly of claim 7, wherein the taper is at least a six degree taper.

10. The injector assembly of claim 7, further comprising: a pressure cap connected to a front wall of the syringe case.

11. The injector assembly of claim 7, wherein the syringe case is formed of molded plastic material.

12. The injector assembly of claim 7, further comprising:
a medical fluid disposed within an internal syringe cavity of the syringe case.

13. The injector assembly of claim 12, wherein the medical fluid is contrast media.

* * * * *